(12) United States Patent
Godara et al.

(10) Patent No.: US 10,321,953 B2
(45) Date of Patent: Jun. 18, 2019

(54) SURGICAL MAPPING TOOLS AND METHODS

(71) Applicant: Medtronic Holding Company Sàrl, Tolochenaz (CH)

(72) Inventors: Neil Godara, Milton (CA); Robert Harrison, Milton (CA)

(73) Assignee: Medtronic Holding Company Sàrl, Tolochenaz (CH)

( * ) Notice: Subject to any disclaimer, the term of this patent is extended or adjusted under 35 U.S.C. 154(b) by 343 days.

(21) Appl. No.: 15/141,043

(22) Filed: Apr. 28, 2016

(65) Prior Publication Data

US 2016/0235471 A1    Aug. 18, 2016

Related U.S. Application Data

(63) Continuation-in-part of application No. 14/852,761, filed on Sep. 14, 2015.

(51) Int. Cl.

| A61B 17/16 | (2006.01) |
|---|---|
| A61B 17/34 | (2006.01) |
| A61B 17/88 | (2006.01) |
| A61B 18/14 | (2006.01) |
| A61B 18/00 | (2006.01) |
| A61B 90/00 | (2016.01) |

(52) U.S. Cl.
CPC ........ A61B 18/148 (2013.01); A61B 17/3472 (2013.01); *A61B 17/16* (2013.01); *A61B 17/8855* (2013.01); *A61B 2018/00339* (2013.01); *A61B 2018/00565* (2013.01); *A61B 2018/00577* (2013.01); *A61B 2090/062* (2016.02); *A61B 2090/0811* (2016.02); *A61B 2090/376* (2016.02); *A61B 2090/3762* (2016.02); *A61B 2090/3937* (2016.02); *A61B 2090/3966* (2016.02)

(58) Field of Classification Search
CPC ........ A61B 18/148; A61B 2018/00339; A61B 2018/00565; A61B 2018/00577; A61B 17/3472; A61B 17/16; A61B 17/885; A61B 2090/0062; A61B 2090/0811; A61B 2090/376; A61B 2090/3762; A61B 2090/3937; A61B 2090/3966
See application file for complete search history.

(56) References Cited

U.S. PATENT DOCUMENTS

| 6,716,216 B1 * | 4/2004 | Boucher ............ A61B 17/1631 606/192 |
|---|---|---|
| 8,728,081 B2 * | 5/2014 | Lauchner ........... A61B 17/8855 604/101.05 |
| 2012/0010624 A1 * | 1/2012 | O'Halloran ........ A61B 17/7097 606/94 |
| 2013/0023881 A1 * | 1/2013 | Cook .................... A61B 17/17 606/80 |

* cited by examiner

*Primary Examiner* — Ronald Hupczey, Jr.

(57) ABSTRACT

A method and apparatus are disclosed for a system that maps the proximal and distal ablation subzones and their respective margins using the tools that are used to access the ablation target wherein the tools have markings to indicate which probe and balloon kyphoplasty (BKP) system or vertebroplasty (VP) system to use. Examples of access tools comprise introducers, stylets, and bone drills. In some embodiments of the system, the probe has a marking indicating which BKP or VP system to use.

19 Claims, 4 Drawing Sheets ved application PCT/

SURGICAL MAPPING TOOLS AND METHODS

CROSS-REFERENCES TO RELATED APPLICATIONS

This application is a continuation-in-part of U.S. application Ser. No. 14/852,761, filed Sep. 14, 2015, which is a continuation-in-part of international application PCT/IB2014/059846, filed Mar. 14, 2014; which claims the benefit of U.S. provisional application 61/786,986, filed Mar. 15, 2013. All of the aforementioned applications are hereby incorporated by reference in their entirety. U.S. application Ser. No. 13/660,353, filed Oct. 25, 2012, and U.S. application Ser. No. 13/643,310, filed Oct. 25, 2012, and now issued as U.S. Pat. No. 9,173,700, are hereby incorporated by reference in their entirety.

BACKGROUND ART

The disclosure relates to electrosurgical probes and associated apparatus. More specifically, the disclosure relates to electrosurgical probes and cementoplasty apparatus, and methods of use thereof.

Current clinical practice includes limited abilities in predicting ablation volumes in ablation procedures. Ablation procedures can be performed using, among other things, radiofrequency (RP) or microwave radiation. In the case of combined ablation and cement injection procedures (cementoplasty), there are currently no significant abilities for demonstrating that the volume of tissue affected by the cement injection can be linked to the volume of tissue affected by the ablation.

In these cases, it would be ideal to predictably measure the volume of tissue to be ablated by the probe, and the volume of tissue intended to be affected by the cementoplasty. For example, if one were to perform ablation prior to cementoplasty, which may include balloon kyphoplasty (BKP) or vertebroplasty (VP), it would be preferable to ablate the entire volume of tissue as well as an extra "safety margin" that would be displaced by the cementoplasty procedure. This would have the benefit of ensuring that live tumor cells are not displaced and thus capable of creating a new tumor site.

Additionally, if a common introducer is used for the ablation probe and vertebtroplasty system, then it would be ideal for the length of the probe, introducer, and BKP system to cooperate such that the introducer need not be repositioned to have the desired effect.

Finally, ablation volumes cannot be imaged using conventional imaging techniques typically used in these types of procedures. Thus, having a means to identify the expectant lesion volume, and providing this information to the physician, allows for appropriate procedural decision making.

DETAILED DESCRIPTION

Figure 1:
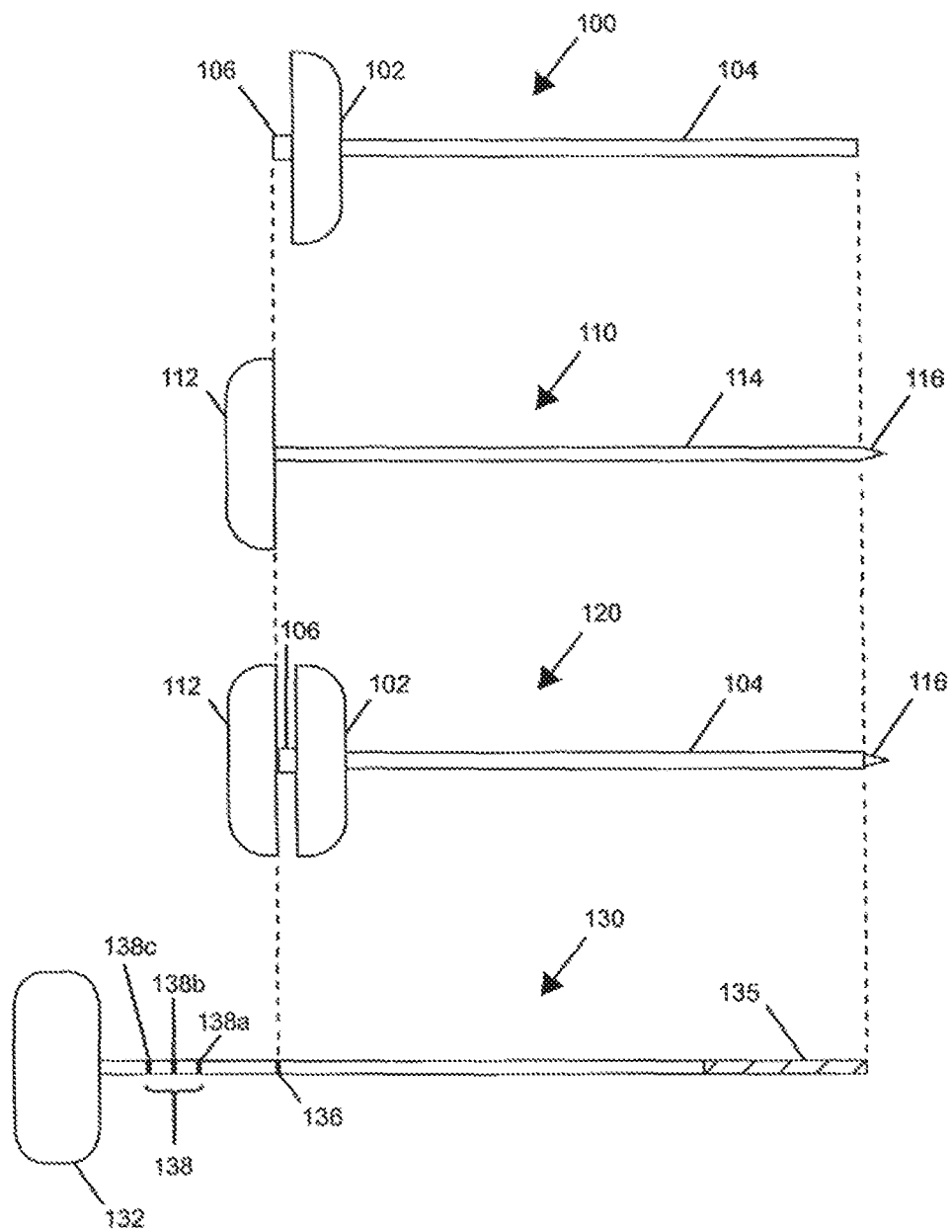
FIG. 1 is an illustration of apparatus used for accessing a treatment site.

The present inventors have conceived and reduced to practice a system wherein tumor ablation is used cooperatively with cementoplasty, including balloon kyphoplasty or vertebroplasty. This invention relates to those cases where both ablation and cementoplasty procedures are performed.

Possible applications include mapping the ablation zone, mapping the cement injection zone, and correlating the two for the proposed benefit, for example, of ensuring that the ablation zone is larger by volume than the cement injection zone, as would be preferable for kyphoplasty, or correlated in some other manner so as to be clinically useful as mandated by patient presentation. Additionally, correlated markings on the mapping components can ensure the use of matched components (i.e. the correct ablation probe and a corresponding inflatable bone tamp, such as a kyphoplasty balloon, are used together).

In one broad aspect, embodiments of the present invention comprise a system that maps the proximal and distal subzones of the desired ablation zone using the tools that are used to access the ablation target and the tools having markings to identify which probe and balloon kyphoplasty system or vertebroplasty system to use. Examples of access tools comprise introducers, stylets, and bone drills.

As a feature of this broad aspect, in some embodiments of the system, the ablation probe has a marking indicating which BKP or VP system to use or which inflatable bone tamp, drill, stylet, or introducer to use to complement that particular probe.

Some embodiments of this broad aspect comprise the following method for performing ablation comprising providing a system that comprises a cannula having a proximal and distal end; a stylet maneuverable within the cannula and having a proximal and distal end, wherein the distal end protrudes beyond the distal end of the cannula; at least one ablation probe; and a drill having a proximal portion with one or more markings and a distal portion which extends beyond the distal end of the cannula. The at least one ablation probe can be used to form an ablation zone which has proximal and distal subzones, wherein a portion of the proximal subzone would have been adjacent to the distal end of the stylet. The drill can be manipulated such that the distal portion of the drill is adjacent to the distal subzone. Some embodiments also comprise a BKP or VP system that is designed to couple with the cannula and have a length such that the zone of effect of the BKP/VP system is complimentary with the ablation zone of the ablation probe.

Other embodiments provide a method for performing ablation and delivering cement comprising providing a system as described herein with an inflatable bone tamp and cement. The at least one ablation probe is used to provide an ablation zone having a volume and having proximal and distal subzones, wherein a portion of the proximal subzone is adjacent to the distal end of the stylet. The drill is manipulated to position the distal portion of the drill adjacent to the distal subzone. A volume of cement less than the volume of the ablation zone can be delivered into a cement injection zone. This cement injection zone can overlap or be entirely enveloped by the ablation zone.

In another broad aspect, embodiments of the present invention comprise a kit comprising; a cannula; a stylet matched to the introducer that protrudes a known distance beyond the introducer; a probe or set of probes for delivering electrical energy and designed to have lengths such that the proximal end of the resultant ablation zones are aligned with the stylet protrusion; a drill that extends beyond the introducer in such a way that a marking on the drill shaft aligns with the introducer whereby the tip of the bone drill identifies the distal extension of the ablation zone created by the probe; and a cementoplasty system that is designed to couple with the introducer and have a length such that the zone of effect of the cementoplasty system is complimentary with the ablation zone of the ablation probe. In typical embodiments, the cementoplasty system comprises a cement delivery system. In some embodiments the cementoplasty system is a balloon kyphoplasty system which comprises an inflatable balloon tamp. In some other embodiments the cementoplasty system is a vertebroplasty system. In some embodiments the kit may comprise a Kirschner wire. Some alternative embodiments do not comprise a stylet, but instead comprise a Kirschner wire.

Some embodiments of this broad aspect comprise a method for performing ablation and delivering cement comprising providing a kit comprising at least one cannula having a proximal and distal portion; at least one stylet maneuverable within the at least one cannula and having a proximal and distal portion, wherein the distal portion protrudes beyond the distal portion of the at least one cannula; at least one ablation probe having a proximal portion and a distal portion; at least one drill having a proximal portion and a distal portion which extends beyond the distal portion of the at least one cannula; at least one inflatable bone tamp; and cement. Each component may have a marking of a certain identity on its proximal portion and the marking of each complementary component has the same identity. The method also comprises using the at least one ablation probe to form an ablation zone having proximal and distal subzones, wherein a portion of the proximal subzone is adjacent to the distal end of the at least one stylet; and manipulating the at least one drill such that the distal portion of the at least one drill is adjacent to the distal subzone.

There also may be embodiments wherein the system further comprises a second stylet and the method further comprises forming a second ablation zone having proximal and distal subzones with a portion of the proximal subzone of the second ablation zone is adjacent to the distal end of the second stylet.

With specific reference now to the drawings in detail, it is stressed that the particulars shown are by way of example and for purposes of illustrative discussion of certain embodiments of the present invention. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The terms "introducer" and "cannula" are used interchangeably in this disclosure, with a "vertebroplasty introducer" and a "kyphoplasty introducer" both being considered to be a type of cannula. Furthermore, the term "introducer assembly" is used to describe a cannula and a stylet that are configured to be used together, for example, introducer assembly 120 comprises a cannula 100 and a stylet 110.

By means of introduction, typical embodiments of the system comprise a cannula 100 of a known length (FIG. 1) that is provided with a stylet 110 that has a known protrusion (i.e. the distal portion of the stylet that extends beyond the cannula when fully inserted therethrough). As seen in FIG. 2, ablation probes 140a to 140c of various lengths are designed to protrude beyond the distal end of the cannula 100 to define a proximal subzone 212 and distal subzone 214 as seen in FIG. 3c. The proximal subzone 212 is the proximal portion of an ablation zone created by delivering energy through the ablation probe. In this way, the user is able to position the stylet tip 116 at the location selected to be adjacent to the space that will be the ablation zone 210.

Figure 2:
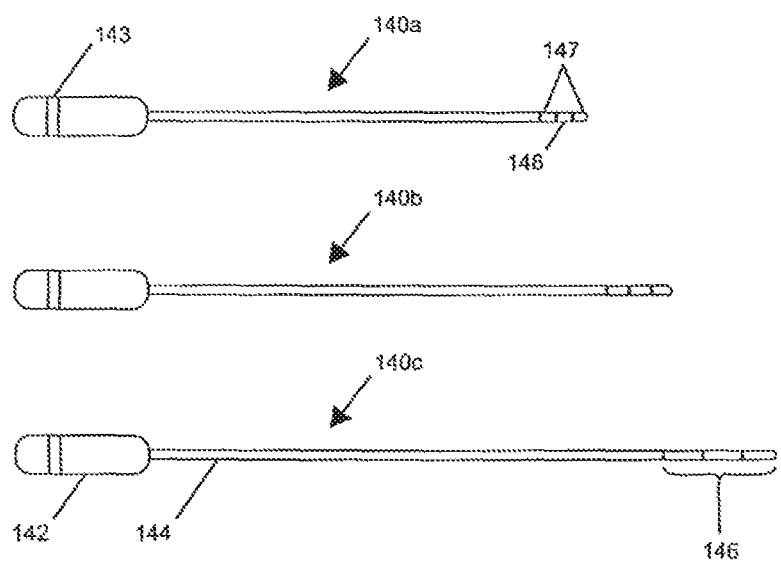
FIG. 2 is an illustration of a set of ablation probes.

The system further comprises a bone drill 130 (FIG. 1). The bone drill is of a known length and extends beyond the introducer. As the bone drill passes through tissue, markings on the proximal portion of the shaft (e.g. probe selection markings 138, FIG. 1) align with the introducer hub. These markings inform the user that the drill has traversed a span of tissue that is correlated to the area to be ablated by the probe (to be explained in more detail below). In a way that is similar to the stylet, the extension of the bone drill and the marking thereon can be used to delineate the distal subzone of the ablation.

The introducer length is also correlated to the length of the BKP or VP system. These systems are designed to couple with the introducer, such that the final position of the systems inside the intended target tissue (and the resultant effect they have) are positionally aligned with the probe extension. The probe (or the associated introductory apparatus) can be provided with markings that help identify the appropriate BKP or VP solution that is matched thereto.

Considering the system and method in greater detail, FIG. 1 illustrates embodiments of the system comprising an introducer assembly 120 comprising a cannula 100 and a stylet 110, and a bone drill 130 which is able to extend through the lumen of the cannula 100 and traverse a distance beyond the distal end of the cannula. A 10 to 13 gauge cannula 100 is typical. The system can be normally used with an imaging system, for example, a fluoroscopic imaging system or a computed tomography (CT) imaging system.

FIG. 2 illustrates a set of probes for delivering electrical energy to tissue, comprising probes 140a, 140b and 140c. Each probe is comprised of a probe handle 142, a probe identifier 143, a probe shaft 144, and an active tip 146 which comprises at least one electrode 147 and at least one section of insulation 148. In the example of FIG. 2, an active tip comprises two electrodes 147 with insulation 148 between the electrodes. In typical embodiments, the probes are operable to deliver energy in a bipolar manner. In the embodiment of FIG. 2, each of the probes has a unique active tip size (length) and would typically correspond with a unique probe ablation zone length, with a probe having a longer active tip expected to produce a larger ablation zone.

FIGS. 3a to 3d illustrate a method of treating tissue for a case in which the target tissue 203 can be ablated with a single energy delivery. The method comprises mapping a proximal subzone 212 and a distal subzone 214 of the desired probe ablation zone 210 (FIG. 3c), which are the outermost boundaries of the area to be ablated, using tools that provide access to the treatment site.

Figure 3A:
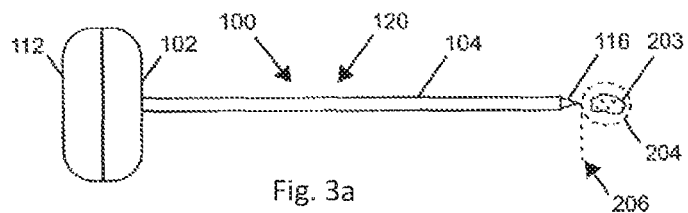
FIGS. 3a to 3f illustrate an embodiment of a method of ablating target tissue and performing cementoplasty.

FIG. 3a illustrates a previously positioned introducer assembly 120 which comprises a cannula 100 containing a stylet 116. Introducer assembly 120 has been advanced and positioned with the distal end of the stylet 116 at proximal subzone 206 of desired ablation zone 204. The positioned distal end of stylet 116 (FIG. 3a) defines the most proximal margin of the proximal subzone 212 (FIG. 3c) and an imaging system can be used to visualize the positioned distal end of the stylet 116 to thereby map the proximal subzone 212. In some cases, for example if target tissue 203 is a tumor, a physician would typically ablate some surrounding tissue to ensure the complete destruction of the target tissue. Accordingly, the desired ablation zone 204 of FIG. 3a includes some tissue that surrounds target tissue 203. Typically, the desired ablation zone 204 corresponds with the portion of tissue an inflatable bone tamp affects and the volume within a cement injection zone.

The method illustrated in FIG. 3 further comprises withdrawing the stylet 116 and replacing it with bone drill 130 as the cannula 100 is in a fixed position. FIG. 3b shows bone drill 130 after it has been advanced into the lumen of cannula 100 wherein a marking on the proximal portion of the bone drill 130 (cannula length marking 136) aligns with a feature of cannula 100 (the proximal end of hub 106) to thereby indicate the distal end of bone drill 130 is at the distal end of cannula 100. FIG. 3b further illustrates that after stylet 110 is withdrawn from cannula 100 there is a gap between the distal end of cannula 100 and desired ablation zone 204.

Figure 3B:
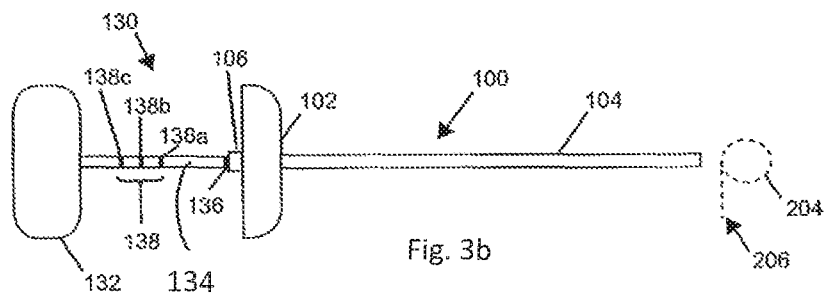
Figure 3C:
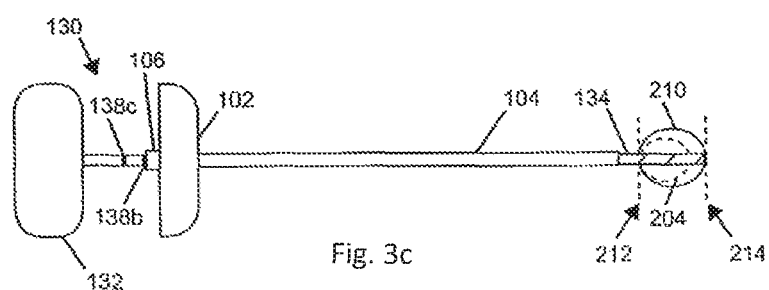

FIG. 3b also illustrates bone drill 130 having three indicia, probe selection markings 138a, 138b, and 138c, which are longitudinally spaced along proximal portion of the bone drill 134. In the illustrated example, bone drill 130 is advanced from the position of FIG. 3b to the position of FIG. 3c in which probe selection marking 138b aligns with a feature of cannula 100, the proximal end of hub 106 of cannula 100. In FIG. 3c, the distal end of bone drill 130 is adjacent to the distal subzone 214 of the probe ablation zone 210. The distal end 130 is imaged to map distal subzone 214. The ablation zone length of the probe is substantially equal to the distance that the distal portion of the bone drill 130 extends beyond the proximal subzone 206 of desired ablation zone 204.

Figure 3D:
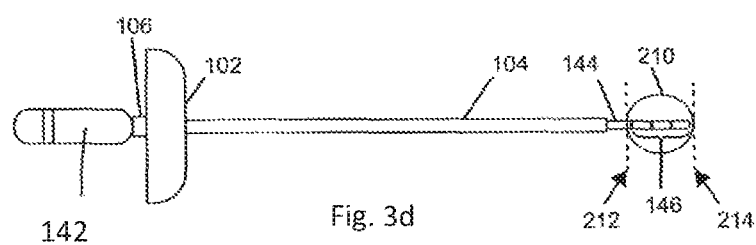

A probe which corresponds with probe selection marking 138b is operable to produce probe ablation zone 210 of the illustrated embodiment. The example of FIG. 3d shows the probe after being inserted into cannula shaft 104 such that probe handle 142 fits against hub 106 and active tip 146 is centered within the probe ablation zone 210. Alternatively, if desired ablation zone 204 is smaller or larger than the example of FIG. 3a, a physician could adjust the position of bone drill 130 such that probe selection marking 138a or 138c lines up with the proximal end of cannula 100, and a probe corresponding selection marking 138a or 138c is selected. A probe corresponding to selection marking 138a has a relatively shorter active tip 146, and a probe corresponding to selection marking 138c has a relatively longer active tip 146. The length of the probe ablation zone mapped using the selected probe selection marking 138 corresponds with the length of the active tip of the selected probe.

After identifying the appropriate probe, the physician withdraws bone drill 130 from the cannula, inserts and positions probe 140 such that probe shaft 144 extends distal of cannula shaft 104 (as shown in FIG. 3d), and delivers energy from active tip 146 to ablate tissue. It is typical that delivering energy from active tip 146 would ablate tissue proximal and distal of active tip 146. FIG. 3d shows probe handle 142, probe shaft 144 and active tip 146 of probe 140 wherein probe handle 142 has been advanced to a stopped position against hub 106 and active tip 146 is centered within probe ablation zone 210 substantially equidistant from proximal subzone 212 and distal subzone 214. In some embodiments that ablation zone 210 is between the proximal subzone 212 and distal subzone 214.

Figure 3E:
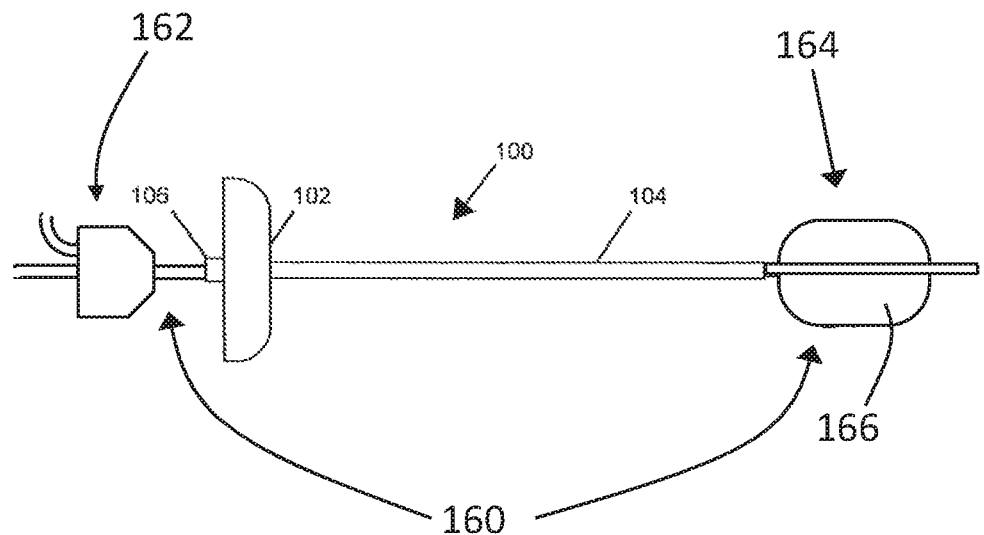

Some embodiments of the method further comprise the use of balloon Kyphoplasty, which can comprise an inflatable bone tamp 160. FIG. 3e illustrates an inflatable bone tamp 160 that has been installed in cannula 100 after the probe has been withdrawn. In typical embodiments of the method, the inflatable bone tamp 160 is selected using marking on the tools used to access the ablation target (e.g. the introducer, stylet 110, and/or bone drill 130) or a marking on probe 140. In some embodiments, the marking is on the packaging for the device contained therein. Inflatable bone tamp 160 comprises a proximal end 162, and a distal end 164 which comprises a kyphoplasty balloon 166, shown as expanded or inflated in FIG. 3e. The balloon 166 is uninflated during advancement of the inflatable bone tamp 160. A fluid is injected into proximal end 162, through the shaft of the system, and into the kyphoplasty balloon 166 for inflation of the balloon. As previously described, the volume of tissue affected by the balloon is substantially similar to the desired ablation volume. By using the inventions described herein, a user is able to determine which balloon to use in order to create an appropriate cavity for cement injection based on the volume of tissue that has been ablated.

Figure 3F:
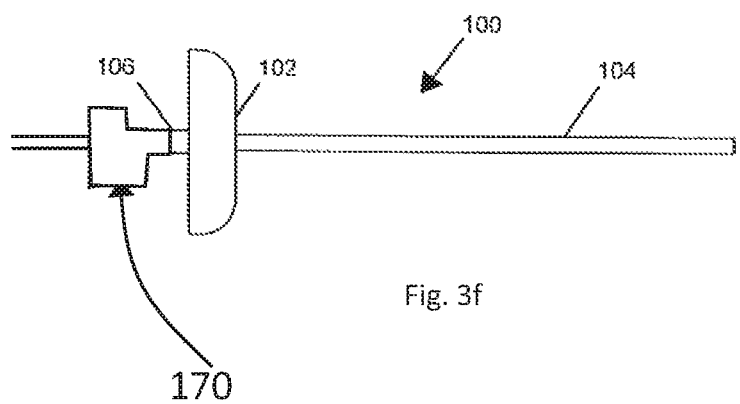

An embodiment of a cement delivery system may then be employed, for both vertebroplasty and kyphoplasty. Typically, markings on the cement delivery system, or packaging thereof, indicate the system is matched to the cannula 100 and probe 140. The cement delivery system has a cement injection zone which is either known or sufficiently known prior to surgery, such that when it is introduced through the cannula 100, the cement injection zone overlaps or rests within the ablation zone. FIG. 3f illustrates cement delivery system 170 connected to the cannula 100. In some embodiments, a Luer lock is used to connect the two. After the connection is made, a selected volume of cement is injected into and through cannula 100, and into the treatment site. Typically, the desired ablation zone 204 comprises at least a portion of the volume and location of desired cement delivery.

In some alternative embodiments, a Kirschner wire (K-wire) is used, upon which other instruments are railed over. In such embodiments, the bone drill and probe(s) have lumens that substantially match the K-wire outer diameter, enabling said instruments to slide over the K-wire. Markings on the K-wire indicate to a user when to stop advancing or withdrawing the bone drill and probe(s). The concepts regarding the use of markings for positioning and device selection also apply to such embodiments.

Embodiments of the present invention comprise a system that maps the proximal and distal ablation subzones and their respective margins using the very tools that are used to access the ablation target wherein the tools having markings to indicate which probe and balloon kyphoplasty system or vertebroplasty system to use. Examples of access tools comprise introducers, stylets, and bone drills. In some embodiments of the system, the probe has a marking indicating which BKP or VP system to use.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

PARTS cannula 100
cannula handle 102
cannula shaft 104
hub 106
stylet 110
stylet handle 112
stylet shaft 114
trocar tip 116
introducer assembly 120
bone drill 130
bone drill handle 132
bone drill shaft 134
helical flutes 135
cannula length marking 136
probe selection markings 138
probe selection marking 138a
probe selection marking 138b
probe selection marking 138c
probe 140
probe 140a
probe 140b
probe 140c
probe handle 142
probe identifier 143
probe shaft 144
146 active tip
electrode 147
insulation 148
fluid connectors 150
fluid tubing 152
electrical connector 154
electrical cable 156
Balloon kyphoplasty system 160
Proximal end 162
Distal end 164
Kyphoplasty balloon 166
cement delivery system 170
target tissue 203
desired ablation volume 204
proximal edge 206
probe ablation zone 210
proximal margin 212
distal margin 214

The invention claimed is:

1. A method for performing ablation of a treatment site and delivering cement to an ablation zone larger than and encompassing the treatment site, the method comprising:
   providing a system that comprises
      a cannula having a proximal end and a distal end, and an interior cavity extending between the proximal end and the distal end;
      a stylet received within the interior cavity of the cannula and having a proximal end and a distal end, wherein the distal end is capable of protruding beyond the distal end of the cannula upon insertion of the stylet into the interior cavity thereof;
      at least one ablation probe having a proximal end and a distal end; and
      a drill having a proximal portion with one or more markings and a distal portion, wherein the distal portion of the drill is capable of extending beyond the distal end of the cannula;
      an inflatable bone tamp with an inflatable balloon; and
      cement;
   inserting portions of the cannula and the stylet received in the interior cavity of the cannula into a human body, and positioning the distal ends of the cannula and the stylet adjacent a proximal margin of a proximal subzone of the ablation zone;
   removing the stylet through the interior cavity of the cannula;
   inserting the drill into and through the interior cavity so that the distal portion of the drill protrudes from the distal end of the cannula;
   manipulating the drill so that the distal portion extends across the ablation zone through the treatment site to adjacent a distal margin of a distal subzone of the ablation zone;
   visualizing the position of the cannula and the stylet during insertion thereof, and visualizing the position of the drill during manipulation thereof;
   removing the drill through the interior cavity of the cannula;
   inserting the ablation probe into and through the interior cavity of the cannula so that the distal end is positioned adjacent the distal margin of the distal subzone;
   using the at least one ablation probe to form the ablation zone substantially between the proximal subzone and the distal subzone;
   removing the ablation probe through the interior cavity of the cannula;
   inserting the bone tamp into and through the interior cavity of the cannula so that the inflatable balloon is positioned within the ablation zone;
   inflating the balloon of the bone tamp;
   removing the bone tamp through the interior cavity of the cannula; and
   delivering a volume of the cement into the ablation zone.

2. The method of claim 1, further comprising manipulating the drill such that one of the one or more markings aligns with a proximal portion of the cannula.

3. The method of claim 1, further comprising a Kirschner wire.

4. The method of claim 1, further comprising a second ablation probe.

5. The method of claim 4, further comprising forming a second ablation zone having a proximal subzone and a distal subzone with the second ablation probe.

6. The method of claim 4, further comprising mapping the distal subzone of the second ablation zone by manipulating the drill and visualizing a position of the distal portion of the drill.

7. The method of claim 1, further comprising a second drill.

8. The method of claim 1, further comprising mapping the ablation zone and mapping a cement injection zone.

9. The method of claim 8, further comprising injecting cement into the cement injection zone.

10. The method of claim 9, wherein the ablation zone is larger by volume than the cement injection zone.

11. The method of claim 1, wherein the ablation probe further comprises a proximal portion and a distal portion, the proximal portion of the ablation probe a marking of a certain identity; wherein the inflatable balloon tamp further comprises a proximal portion and a distal portion, the proximal portion of the inflatable balloon tamp comprising a marking of a certain identity; and wherein all markings of a certain identity have the same identity.

12. The method of claim 1, further comprising mapping the proximal subzone of the ablation zone by visualizing a position of the distal end of the stylet and mapping the distal subzone of the ablation zone by visualizing a position of the distal portion of the drill.

13. A method for performing ablation of a treatment site and delivering cement to an ablation zone larger than and encompassing the treatment site, the method comprising:
   providing a system that comprises
      a cannula having a proximal end and a distal end, and an interior cavity extending between the proximal end and the distal end,
      a stylet maneuverable within the interior cavity of the cannula and having a proximal end and a distal end, wherein the distal end is capable of protruding beyond the distal end of the cannula upon insertion of the stylet into the interior cavity thereof,
      at least one ablation probe having a proximal end and a distal end,
      a drill having a proximal portion with a marking and a distal portion, wherein the distal portion of the drill is capable of extending beyond the distal end of the cannula,
      an inflatable bone tamp with an inflatable balloon, and cement;
   inserting the stylet into and through the interior cavity of the cannula so that the distal end of stylet protrudes from distal end of the cannula;
   after insertion of the stylet, inserting portions of the cannula and the stylet into a human body, and positioning the distal ends of the cannula and the stylet adjacent a proximal margin of a proximal subzone of the ablation zone;
   removing the stylet through the interior cavity of the cannula, and inserting the drill into and through the interior cavity so that the distal portion of the drill protrudes from the distal end of the cannula;
   after removal of the stylet and insertion of the drill, manipulating the drill so that the distal portion extends across the ablation zone through the treatment site to adjacent a distal margin of a distal subzone of the ablation zone;
   visualizing the position of the cannula and the stylet during insertion thereof, and visualizing the position of the drill during manipulation thereof;
   removing the drill through the interior cavity of the cannula, and inserting the ablation probe into and through the interior cavity of the cannula so that the distal end is positioned adjacent the distal margin of the distal subzone;
   using the at least one ablation probe to ablate tissue including the treatment site in the ablation zone;
   removing the ablation probe through the interior cavity of the cannula, and inserting the bone tamp into and through the interior cavity of the cannula so that the inflatable balloon is positioned within the ablation zone;
   inflating the balloon of the bone tamp;
   removing the bone tamp through the interior cavity of the cannula; and
   delivering a volume of the cement less than the volume of the ablation zone through the interior cavity of the cannula and into a cement injection zone, a portion of the cement injection zone at least partially overlapping the ablation zone.

14. The method of claim 13, wherein the system further comprises a second ablation probe and the method further comprises using the second ablation probe to form a second ablation zone having a second volume and having a proximal subzone and a distal subzone and delivering a second volume of cement into a second cement injection zone, a portion of which at least partially overlaps the second ablation zone.

15. The method of claim 13, wherein the ablation probe further comprises a proximal portion and a distal portion, the proximal portion of the ablation probe comprising a marking of a certain identity; wherein the inflatable balloon tamp further comprises a proximal portion and a distal portion, the proximal portion of the inflatable balloon tamp comprising a marking of a certain identity; and wherein all markings of a certain identity have the same identity.

16. The method of claim 13, further comprising mapping the proximal subzone of the ablation zone by visualizing a position of the distal end of the stylet and mapping the distal subzone of the ablation zone by visualizing a position of the distal portion of the drill.

17. The method of claim 13, further comprising a second ablation probe.

18. The method of claim 17, further comprising forming a second ablation zone having a proximal subzone and a distal subzone with the second ablation probe.

19. The method of claim 18, further comprising mapping the distal subzone of the second ablation zone by manipulating the drill and visualizing a position of the distal portion of the drill.

* * * * *